(12) United States Patent
Callaghan et al.

(10) Patent No.: US 12,181,385 B2
(45) Date of Patent: Dec. 31, 2024

(54) MANUAL METHOD FOR DEPOSITING A SAMPLE DIRECTLY ONTO A SLIDE FOR LIQUID BASED CYTOLOGY

(71) Applicant: BECTON DICKINSON AND COMPANY, Franklin Lakes, NJ (US)

(72) Inventors: Ryan Callaghan, Raleigh, NC (US);
Clark M Whitehead, Cary, NC (US);
William Alan Fox, Whitsett, NC (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 828 days.

(21) Appl. No.: 16/632,060

(22) PCT Filed: Jul. 18, 2018

(86) PCT No.: PCT/US2018/042693
§ 371 (c)(1),
(2) Date: Jan. 17, 2020

(87) PCT Pub. No.: WO2019/018527
PCT Pub. Date: Jan. 24, 2019

(65) Prior Publication Data
US 2020/0150008 A1    May 14, 2020

Related U.S. Application Data

(60) Provisional application No. 62/534,841, filed on Jul. 20, 2017.

(51) Int. Cl.
*G01N 1/30* (2006.01)
*G01N 1/28* (2006.01)
(Continued)

(52) U.S. Cl.
CPC ............ *G01N 1/2813* (2013.01); *G01N 1/30* (2013.01); *G01N 1/312* (2013.01); *G01N 2001/2846* (2013.01); *G02B 21/34* (2013.01)

(58) Field of Classification Search
CPC ........ G02B 21/34; G01N 1/2813; G01N 1/30; G01N 1/312; G01N 2001/2846
See application file for complete search history.

(56) References Cited

U.S. PATENT DOCUMENTS 5,419,279 A * 5/1995 Carrico, Jr. .......... G01N 1/2813
                                                          118/421
6,627,158 B1   9/2003 Peltier
(Continued)

FOREIGN PATENT DOCUMENTS

CN        104931316 A      9/2015
CN        106124266 A     11/2016
(Continued)

OTHER PUBLICATIONS

Office Action from corresponding Chinese Application No. 201880057988.1 dated Sep. 22, 2022 (16 pages).
(Continued)

*Primary Examiner* — Abigail Vanhorn
*Assistant Examiner* — Mary A Crum
(74) *Attorney, Agent, or Firm* — Botos Churchill IP Law LLP

(57) ABSTRACT

A biological sample is provided, wherein the biological sample is a liquid-based cytology sample. A slide is placed in a holder. The slide is pre-coated with a composition that will cause cells to adhere to the slide. A settling chamber is placed over the slide and the settling chamber is locked onto the holder. The settling chamber has openings in both proximate and distal ends. The opening in the distal end of the settling chamber is positioned over the slide. A density reagent is then dispensed into the settling chamber. The liquid-based cytology sample is then dispensed into the settling chamber over the reagent. The assembly formed by the holder, slide and settling chamber (and its liquid contents) is placed in a centrifuge. The density reagent and the liquid thereover are decanted from the settling chamber. The settling chamber is removed from over the slide.

13 Claims, 14 Drawing Sheets

(51) Int. Cl.
*G01N 1/31* (2006.01)
*G02B 21/34* (2006.01)

(56) References Cited

U.S. PATENT DOCUMENTS

| | | |
|---|---|---|
| 2003/0175850 A1 | 9/2003 | Ross et al. |
| 2003/0228705 A1 | 12/2003 | Chan et al. |
| 2013/0045852 A1 | 2/2013 | Chapman et al. |
| 2013/0116102 A1* | 5/2013 | Hansen .................. B01D 43/00 494/10 |

FOREIGN PATENT DOCUMENTS

| | | | | |
|---|---|---|---|---|
| EP | 2244083 A1 * | 10/2010 | ........... | G01N 1/2813 |
| WO | WO-2006034385 A1 * | 3/2006 | .............. | C12M 1/00 |

OTHER PUBLICATIONS

International Search Report issued in corresponding PCT application No. PCT/US2018/042693 on Oct. 29, 2018.
Office action from corresponding Indian Application No. 202017003189 dated Dec. 8, 2022, 6 pp.
Office Action issued in corresponding Australian Patent Application No. 2018302151 dated May 3, 2023 (3 pp.).
Office Action issued in corresponding Chinese Patent Application No. 2018800579881 dated Mar. 16, 2023 (21 pp.).

* cited by examiner

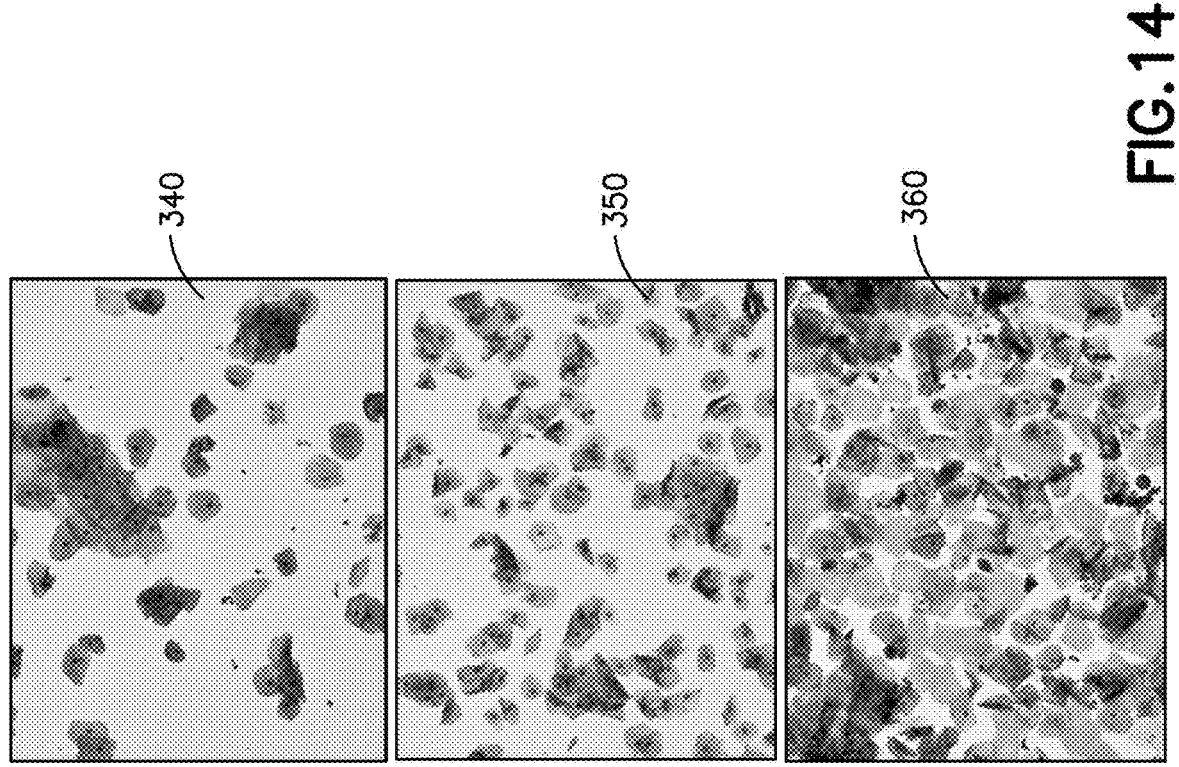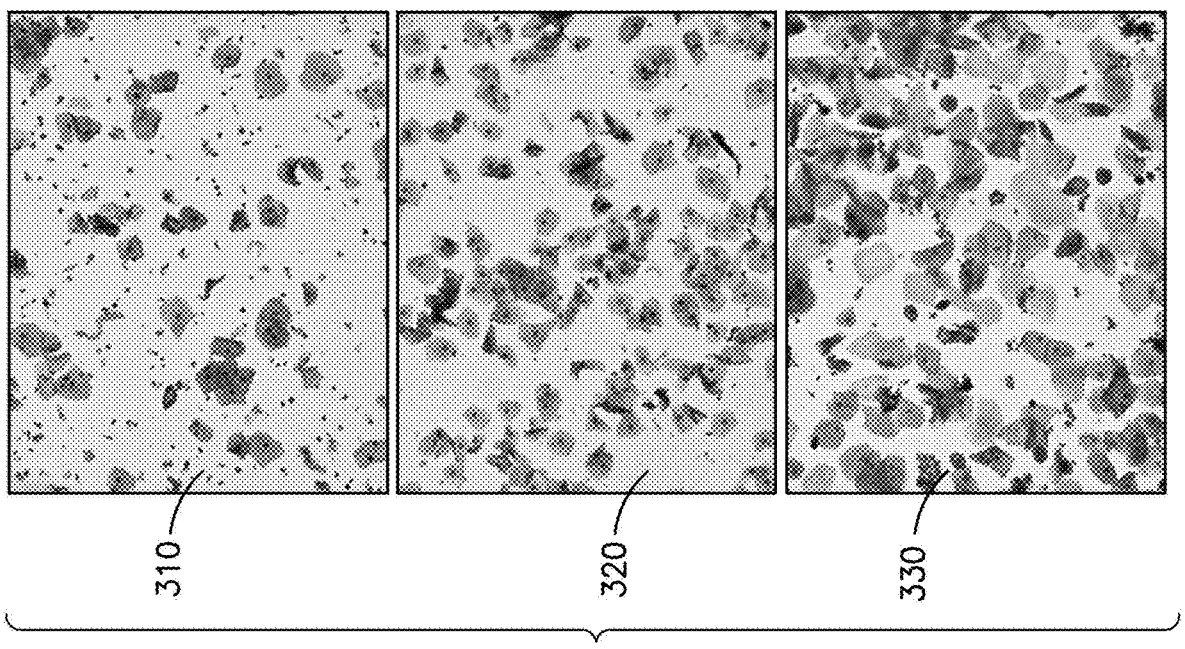
FIG. 14

MANUAL METHOD FOR DEPOSITING A SAMPLE DIRECTLY ONTO A SLIDE FOR LIQUID BASED CYTOLOGY

CROSS REFERENCE TO RELATED APPLICATIONS

The present application is a national phase entry under 35 U.S.C. § 371 of International Application No. PCT/US2018/042693, filed Jul. 18, 2018, which claims the benefit of the filing date of U.S. Provisional Patent Application No. 62/534,841, filed Jul. 20, 2017 the disclosures of which are incorporated by reference herein.

TECHNICAL FIELD

The present invention is directed to depositing samples on slides for liquid-based cytology (LBC).

BACKGROUND

Cancer kills over 8 million people every year, accounting for approximately 13% of deaths globally, mostly from the Asia Pacific. Cytology has been fast and minimally invasive form for detection of cancer; the screening is a fast, minimally invasive, widely accepted method and has reduced the incidence of cervical cancer in countries with organized screening. Several methods have been introduced over the past decade, namely LBC and molecular testing. For example, current cervical cancer screening cytology processing methods require expensive instrumentation and support infrastructure. As such, cost concerns, quality, sensitivity and reproducibility of cytology results are of critical concern in the developing world. The development/discovery of simple streamlined, cost efficient methods of cytology preparation is a substantial unmet clinical need.

One of the challenges for automated screening is the preparation of the cellular smear onto the slide. As noted in U.S. Pat. No. 5,436,831 to Carrico, C., Jr. et al., for automated screening of cytology samples, a monolayer of cytological material on an optically-clear, cationically charged substrate is desirable. Cytology samples of variable thickness or with cell overlap are problematic in automated processes that require a standardized and well-controlled specimen preparation procedure. Carrico et al. describes separating cytological material by centrifugation over a density gradient, thereby producing a packed pellet of cytological material. The packed pellet is then mixed with a diluent and an aliquot of the suspension is placed in a sedimentation vessel attached to a microscope slide. The negatively-charged cells in the suspension are attracted to the cationically-charged slide and the cells settle onto the underlying slide without centrifugation. The excess of the suspension is aspirated leaving a monolayer of suspension on the slide. U.S. Pat. No. 5,419,279 to Carrico, C., Jr. et al., describes a sedimentation vessel for depositing and staining cytological material on a microscopic slide. The sedimentation vessel is illustrated in FIG. 1. Reference numeral 12 indicates a side wall of an elongated hollow tube 10, which side wall 12 defines an inner chamber 14. The inner diameter of the tube 10 is less than the width of the microscope slide onto which is to be placed. The tube 10 also includes a pair of outwardly-extending connector flanges 16 that are integrally formed with a base member 20 which is disposed at the bottom end of the side wall 12. The base member 20 is disk-shaped. The base member 20 provides structural support to the tube 10. It is apparent that a disk-shaped, or any other shaped base, is not necessary for the practice of the apparatus of the invention. As shown in FIG. 1, the base member 20 has a diameter greater than the diameter of the cylindrical side wall 12. FIG. 1 also shows that the outwardly-extending connector flanges 16 are each provided with a guide flange 18 positioned at the terminal end of the flange 16. Each guide flange 18 is substantially perpendicularly disposed to the connector flange 16, thus forming a shape resembling the letter "L". A sealing member 22, such as an O-ring, is disposed at the bottom end of the tube 10 where the tube abuts the surface of the microscope slide 24.

The base plate 26, as shown in FIG. 1, comprises a recessed area 29 which receives and confines a microscope slide 24. The recessed area 29 is configured and dimensioned to conform to the shape of a microscope slide such that when a slide is placed on the flat surface in the recessed area 29, it is prevented from substantial side-to-side or end-to-end movement. This facilitates cell deposition and staining on a series of slides which have cell collections located in approximately the same location on the slides, which then promotes the use of the slides on automated slide analyzing equipment. The base plate 26 also includes slots 28a, 28b that extend outwardly from the recessed area 29 and which slots 28a, 28b receive the outwardly-extending connector flanges 16. Formed within each slot 28a, 28b is a passage 30 which is preferably formed substantially parallel to the flat surface of recessed area 29. Each slot 28a, 28b and passage 30 is configured and dimensioned to receive and releasably securely hold a connector flange 16, and a guide flange 18 when the tube 10 is rotated when disposed in the base plate 26. The sedimentation vessel is open at the top to receive the suspension and open at the bottom where it abuts the slide.

U.S. Pat. No. 8,617,895 to Fox et al. describes the use of pre-coated slides to immobilize a sample thereon. The substrates are coated with a polycationic polymeric coating with long shelf life. The polycationic coating assists in immobilizing biological samples having a net negative charge (e.g. tissue samples) on the coated substrate.

Modern technology has allowed for the development of advanced and highly automated processes for preparing LBC samples. However, in certain parts of the world, automated processes are not feasible because of their higher cost of implementation and development. Therefore efficient, reproducible, low-cost methods for preparing LBC samples that can rival automated methods in terms of reliability and accuracy continue to be sought.

SUMMARY

Described herein is a manual method for directly enriching and depositing a liquid-based cytology sample on a slide using a simple one step process. According to the method, the sample vial is first agitated. Agitation is performed using a conventional sample vortexer. A pre-coated slide is provided which is positioned into a slide holder. A settling chamber is then affixed to the slide, the slide being held in place by the slide holder. A density reagent is then added to the settling chamber. The sample is then applied over the density reagent. The complete assembly of the slide, slide holder and settling chamber carrying the density reagent and the sample is then placed into a centrifuge. After centrifugation, the assembly is removed from the centrifuge and is inverted. Unwanted material and the density reagent are decanted from the slide. The slides are pre-coated with a material that causes the cytology sample to adhere to the slide when deposited thereon. One example of a pre-coated slide suitable for use in the present process is the SURE-PATH® PreCoat slide from Becton Dickinson. The slide is then ready to be stained according to known cytologic staining protocols. The method described herein contemplates that the prepared slide can be stained by any accepted staining protocol.

Described herein is a method for preparing a cytology sample for staining. The manual method includes: i) providing a biological sample, where the biological sample is a liquid-based cytology (LBC) sample; ii) disposing a pre-coated slide in a holder adapted for receiving the pre-coated slide, the slide pre-coated with a composition that will cause cells to adhere to the pre-coated slide; iii) placing a settling chamber over the pre-coated slide and locking the settling chamber onto the holder wherein the settling chamber has openings in both proximate and distal ends. The opening in the distal end is positioned over the pre-coated slide such that the pre-coated slide is interposed between the holder and the settling chamber and the pre-coated slide is in fluid communication with the settling chamber. The settling chamber is then locked into place in the holder thereby forming an assembly of the holder, the pre-coated slide and the settling chamber. A density reagent is then dispensed into the settling chamber after which the liquid-based cytology sample is dispensed into the settling chamber over the density reagent. The amount of the liquid-based cytology sample placed in the settling chamber is about 1 mL to about 2 mL. The amount of the density reagent is about 1 to about 4 ml. The assembly is then placed in a centrifuge. The method also includes centrifuging the assembly for about 5 minutes or less at a rotation force of about 500 g or less. Embodiments of the method include decanting the density reagent and the liquid-based cytology sample thereover from the settling chamber, after which the settling chamber is removed from over the pre-coated slide and staining the sample on the pre-coated slide.

In a further embodiment the assembly is centrifuged for about 0.5 to about 5 min at a rotation force of about 50 g to about 500 g. In yet a further embodiment the assembly is centrifuged for about 0.5 minutes to about 5 minutes at a rotation force of about 50 g to about 250 g. In a further embodiment the assembly is centrifuged for about 2 to about 3 minutes at a rotation force of about 200 g. In a further embodiment the assembly is centrifuged for about 5 minutes at a rotation force of about 50 g. In a further embodiment the assembly is centrifuged for about 2 to about 5 minutes at a rotation force of about 100 g. In a further embodiment the assembly is centrifuged for about 2 to 5 minutes at a force of about 200 g. In a further embodiment the assembly is centrifuged for about 1 minute to about 3 minutes at a force of about 250 g. Examples of a suitable pre-coated slide is a slide pre-coated with a polycationic coating. Examples of such polycationic coatings are non-peptidic, quaternary ammonium polymer coatings. One example of a non-peptidic, quaternary ammonium polymer is polydiallydimethylammonium (PDDA).

BRIEF DESCRIPTION OF DRAWINGS

FIG. 14 compares stained samples on slides prepared using the process outlined in FIG. 3 with stained samples on slides prepared using the process of FIG. 2.

DETAILED DESCRIPTION

Figure 1:
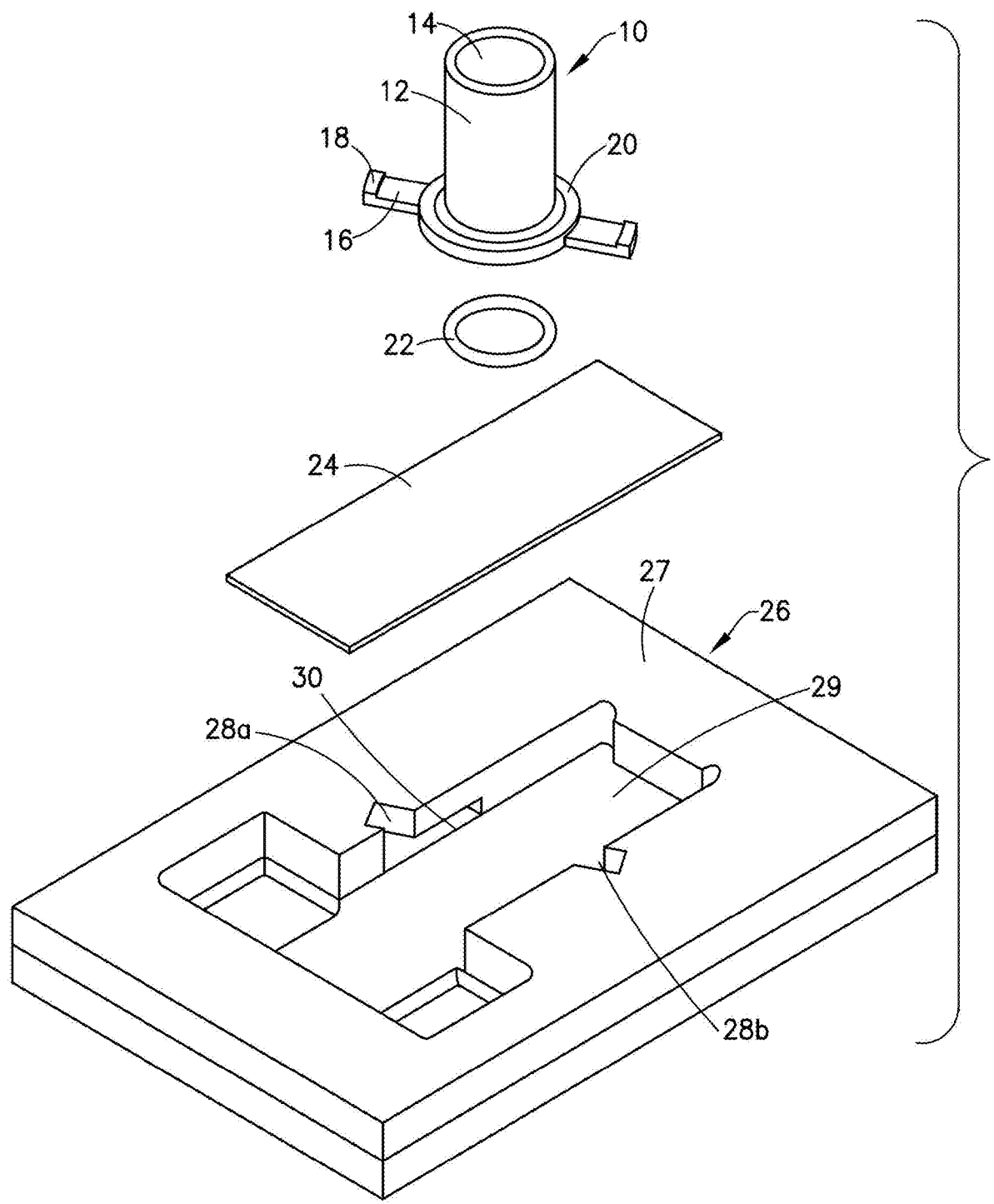
FIG. 1 illustrates a prior art assembly for preparing cytology samples.

Embodiments are described in detail herein with reference to the drawing figures wherein like reference numerals identify similar or identical elements. It is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Prior art methods and apparatus for staining cytological material on a microscope slide are described in U.S. Pat. No. 5,419,279 to C. Carrico, Jr. et al., which is incorporated by reference. The apparatus described in U.S. Pat. No. 5,419,279 includes a hollow tube with flanges that extend from the base therefrom that engage a base member. The base member has a base plate the receives the slide.

Figure 2:
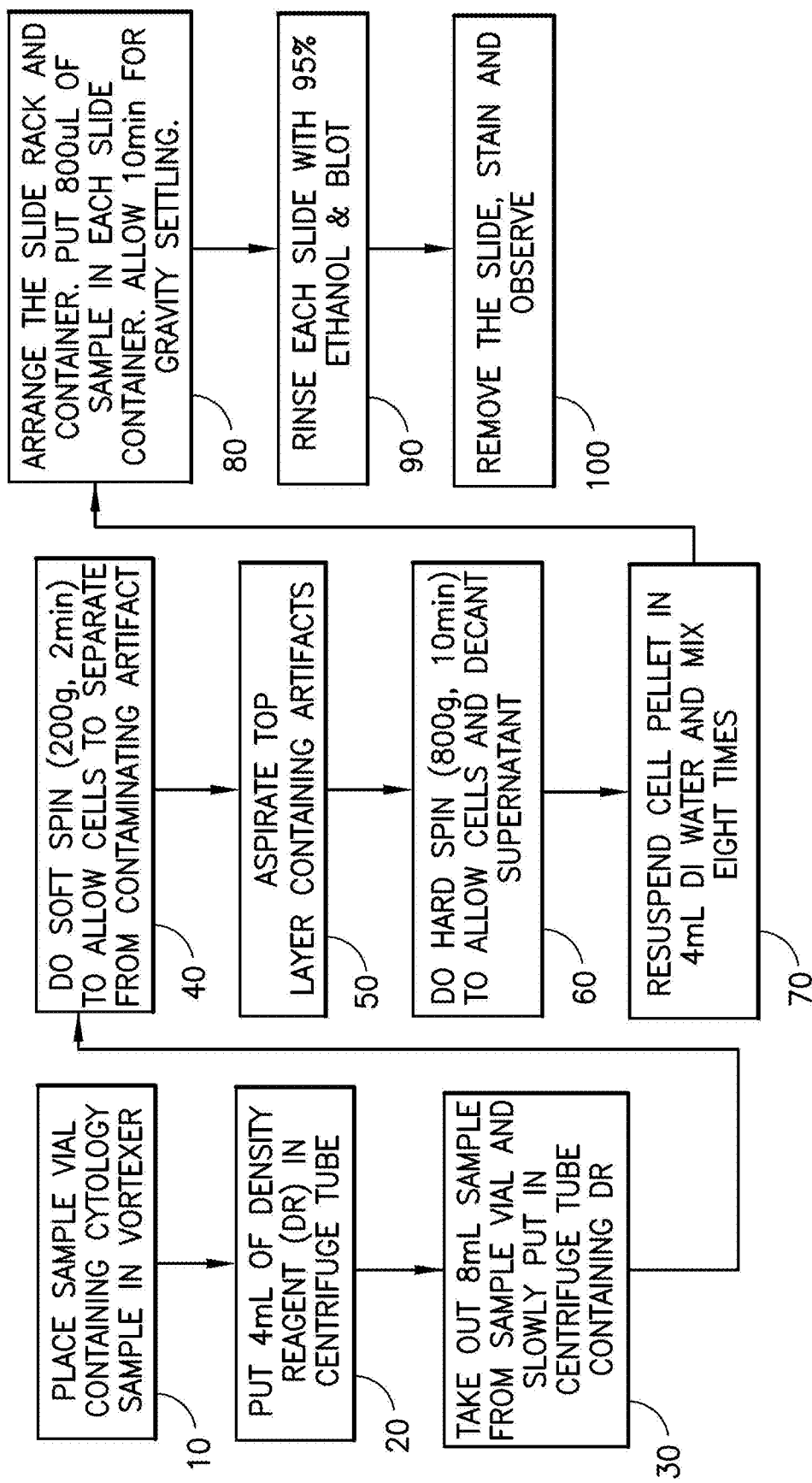
FIG. 2 illustrates a prior art process for preparing cytology samples.

Methods for producing a monolayer of cytological material on an optically-clear, cationically-charged substrate are described in U.S. Pat. No. 5,346,831 to C. Carrico Jr. et al., which is incorporated by reference herein. One example of a prior art method is illustrated in FIG. 2. The illustrated method is illustrated as having ten steps. In step 10, the sample vial containing the sample is placed in a vortexer to ensure that the sample is homogeneous. The sample is typically carried in a collection device combined with preservatives, transport reagents etc. In step 20, a density reagent (4 mL) is dispensed into a centrifuge tube. In step 30, sample (8 mL) is aspirated from the sample vial and dispensed into the centrifuge tube containing the density reagent. In step 40, the centrifuge tube is subjected to a "soft" spin (e.g. 200 g for 2 minutes). In step 50, the unwanted portion of the sample (i.e. the non-cellular constituents) remains on top of the density gradient and is aspirated or otherwise removed from the centrifuge tube. In step 60, the centrifuge tube is placed back into the centrifuge and centrifuged at a speed faster than the centrifuge speed for the soft spin and for a time longer than the time for the soft spin (e.g., 800 g for ten (10) minutes). Such centrifugation conditions are referred to as a hard spin. Excess fluid (i.e. the supernatant) is removed and the centrifuge tube and the remaining sample is in the form of a cell pellet. In step 70 the cell pellet is resuspended in DI water (4 mL) and mixed eight times. In step 80, the sample is deposited on each slide in an array of slides carried by a slide rack. The slides are pre-coated with material that will cause the cellular material to adhere to the slide. Examples of such slides are described herein. In step 90, the slides are rinsed with an alcohol solution (e.g. 95% alcohol). In step 100, the slides are then removed from the slide rack and stained according to conventional practices well known to those skilled in the art and not described in detail herein.

Other prior art methods for forming a liquid-based cytology sample on a slide use a syringe/filter assembly or a dual flow cassette. These methods do not require centrifugation. However, these methods employ apparatus that have filters, which may lose cells when depositing cells onto slides.

Figure 3:
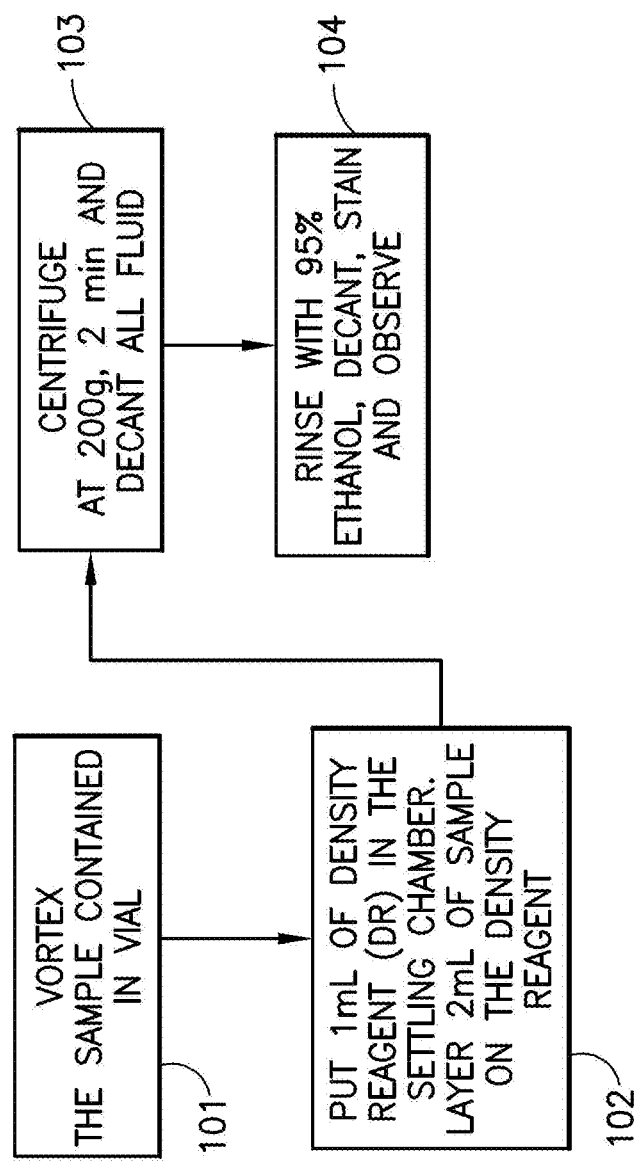
FIG. 3 illustrates one embodiment of the process described herein.

A flow chart for the new and useful method described herein is illustrated in FIG. 3. In one embodiment of the new and useful method described herein, in step 101, the sample vial is vortexed just as described in the prior art method. However, after vortexing, the sample (2 mL) is placed in a settling chamber disposed over a slide carried by a holder in step 102. The slide is pre-coated with a substance that causes the cellular material to adhere to the slide. Such substances are known to those skilled in the art and are not described in detail herein. The settling chamber contains a density reagent (1 mL). Density reagents are well known to one skilled in the art and not described in detail herein. The assembly of settling chamber (with sample and density reagent disposed therein), slide and holder are placed in a centrifuge and subjected to a soft spin (200 g for 2 minutes) in step 103. In step 104 the liquid contents in the settling chamber are decanted and the slides are then rinsed with an alcohol solution (e.g. 95% ethanol or equivalent alcohol blend) and then stained according to conventional practice so that the sample can be evaluated. The above method reduces the steps in the prior art method by half and can be practiced with fewer handling steps and therefore more easily practiced as a manual method compared with prior art method.

Figure 4:
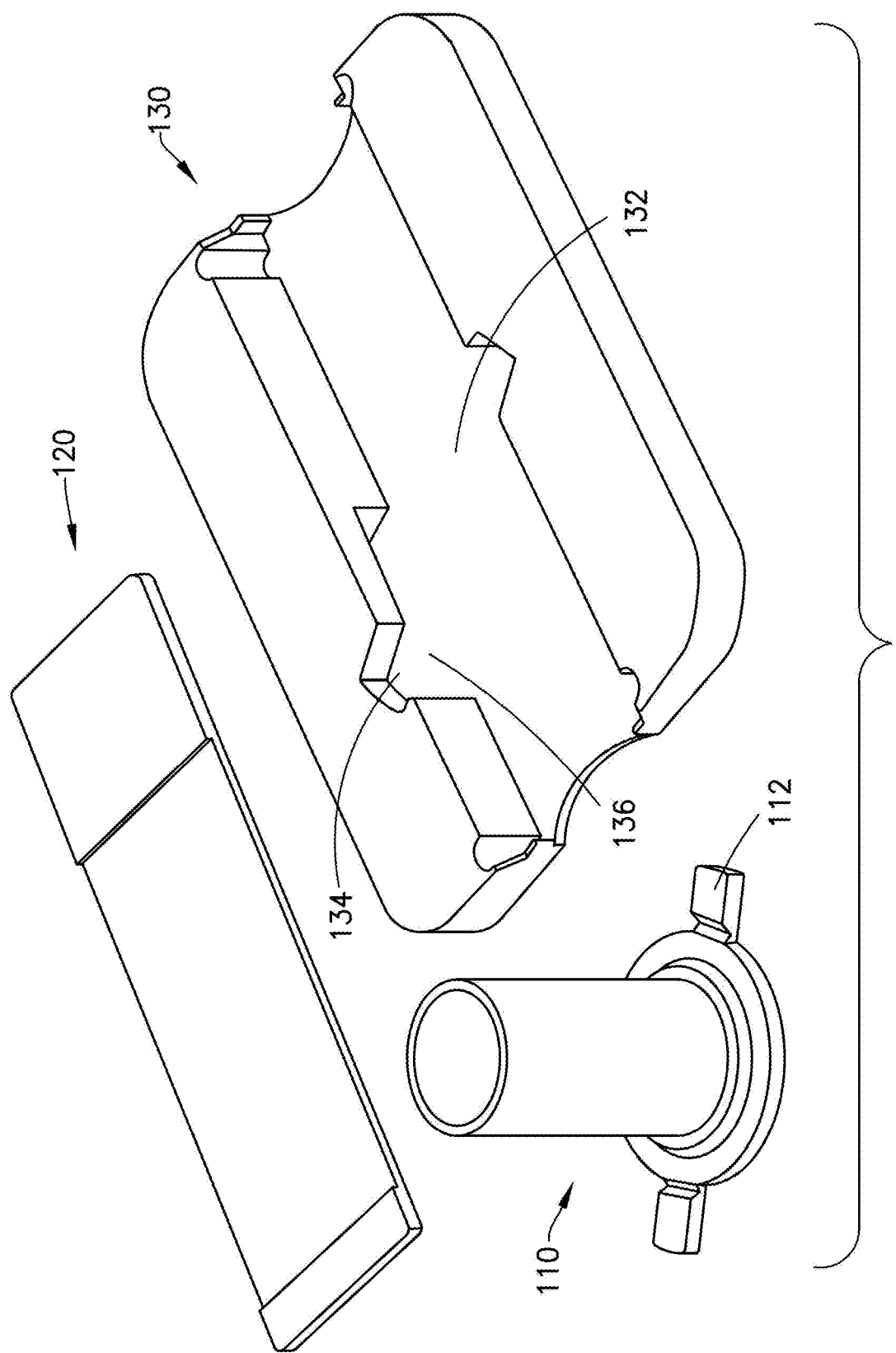
FIG. 4 illustrates the individual components of the slide holder that couples the slide with the settling chamber according to the method.
Figure 5:
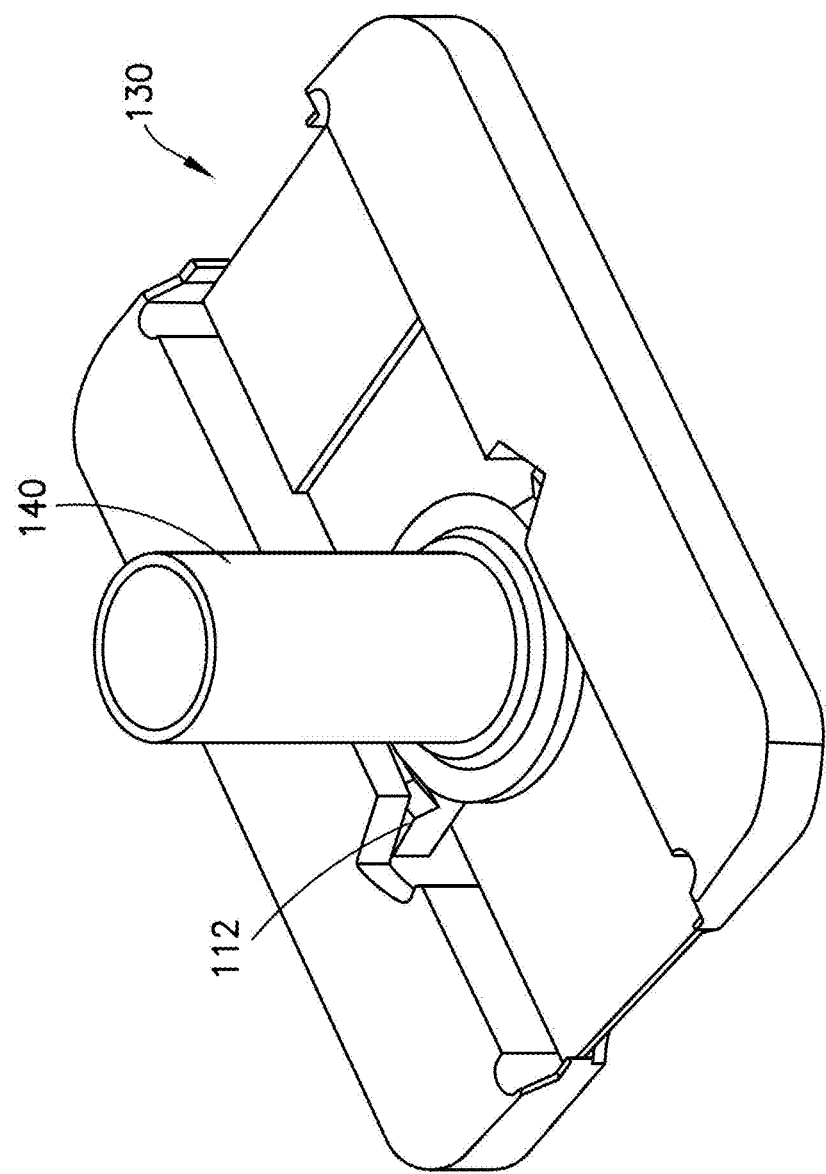
FIG. 5 illustrates the slide and settling chamber coupled together in the holder.

Referring to FIGS. 4 and 5, in one embodiment a settling chamber 110 is assembled with a slide 120 in holder 130 to form assembly 140. The slide is a pre-coated BD PreCoat™ Slide that is obtained commercially from Becton Dickinson (BD). Pre-coated slides used to immobilize sample on a slide are known to those skilled in the art and are not described in detail herein. Examples of such slides are described in U.S. Pat. No. 8,617,895 to W. Fox et al., which is incorporated by reference herein. According to another embodiment of the invention, the non-peptidic polymeric material used for coating the pre-coated substrate includes an allylic polymer, a vinylic polymer, or a combination thereof, preferentially having cationic groups selected from the group consisting of primary amines, secondary amines, tertiary amines, and quaternary amines. Among the examples of polycationic coatings described in the '895 Patent are non-peptidic, quaternary polymers ammonium such as, for example, polydiallydimethylammonium (PDDA). Another example of a suitable non-peptidic polymeric material is polyallylamine (PAA). Suitable slide pre-coatings that carry cationic groups for attracting negatively charged sample onto the slide are well known to one skilled in the art and not described in detail herein.

Figure 13:
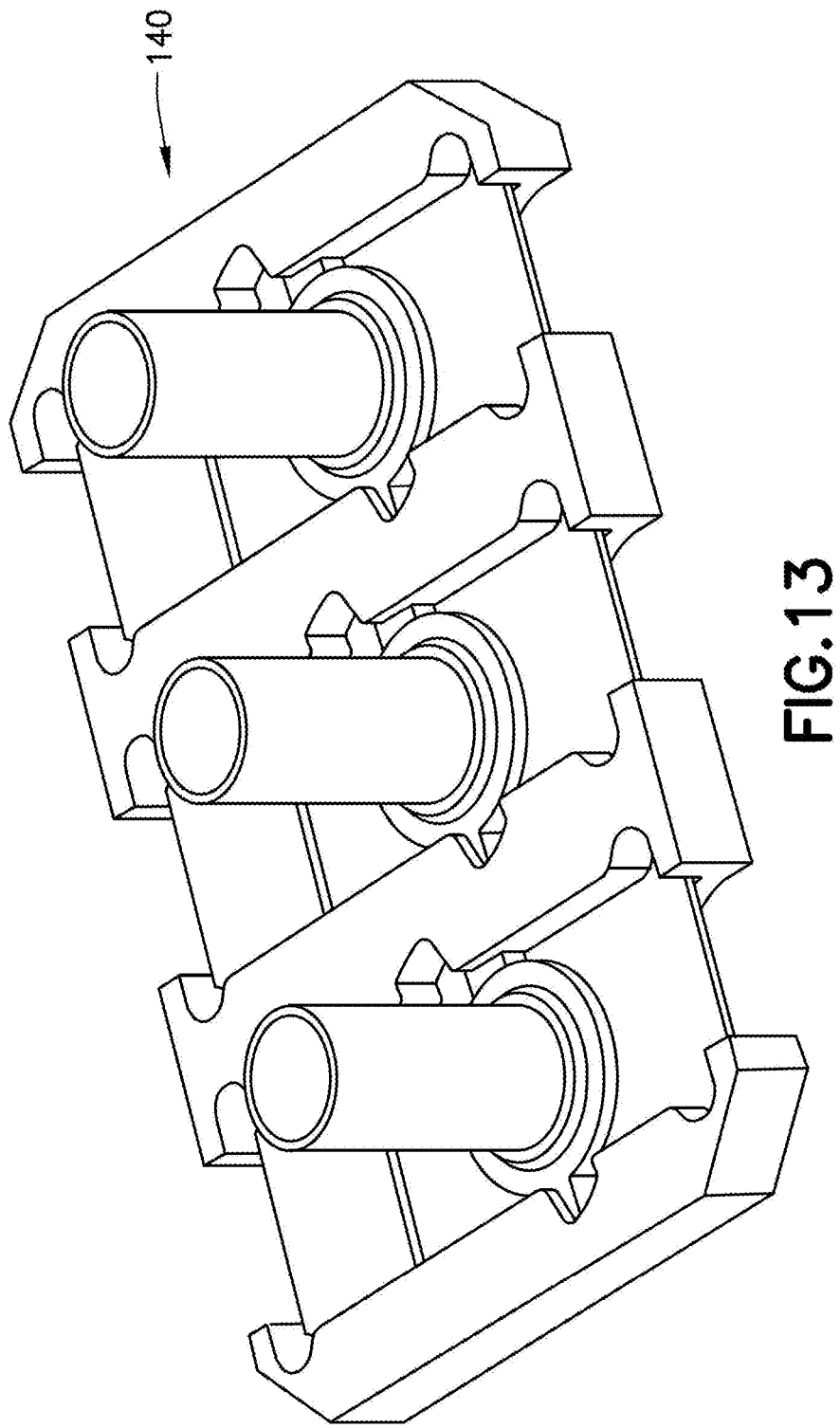
FIG. 13 illustrates multiple holder assemblies coupled together.

Such slides carry a coating that cause the cellular sample to adhere to the slide. The slide holder 130 is adapted to receive the slide 120 on a slide platform 132. The slide holder 130 has slots 134 that will receive tabs 112 on the settling chamber 110. Rotating the settling chamber will cause the tabs 112 to rotate into channels 136 thereby securing the settling chamber 110 in the holder 130. The tab 112 locked into engagement with the holder 130 is illustrated in FIG. 4. FIG. 13 illustrates an assembly 140 that can receive three slides/settling chambers. The assembly illustrated in FIG. 13 is compatible with standard microtiter plate centrifuge holders.

In one embodiment of the direct to slide process described herein a pre-coated slide is labeled with a specimen number associated with a specimen that has been accessioned into the lab. After the slide is labeled it is inserted into the slide holder as illustrated in FIGS. 4 and 5.

In one embodiment of the method described herein, the sample is received into the laboratory and assigned an accession number. The samples are received in a format suited for LBC. One such format is a sample carried in a preservative (SurePath™ Preservative) fluid collection vial. A slide (e.g. a BD PreCoat™ Slide) is labeled with the accession number. The slide is then placed into a holder such as the holder illustrated in FIG. 4. A settling chamber is locked onto each slide as illustrated in FIG. 5. SurePath™, PreCoat™, PrepStain® are all trademarks of Becton Dickinson and Company (BD).

Density Reagent (for example, BD Density Reagent®; 1 mL) is added to at least one settling chamber. The amount of density reagent can vary as one skilled in the art is aware. The skilled person will select the amount of density reagent suited for their particular application. Amounts of density reagents in the range of about 1 mL to about 2 mL are contemplated as suitable. Sample is then added to the settling chamber, but, prior to adding the sample to the settling chamber, each sample container is vortexed for about 10 to about 15 seconds (at 3000 rpm). The cap on the sample container is removed and sample (for example, 2 mL) is aspirated from the container using a standard pipettor. In the method described herein, the sample volume is about 1 mL to about 2 mL. The sample is dispensed from the pipette tip by placing it firmly against the inside of the settling chamber, and just above the Density Reagent. Dispensed in this way, the sample layer forms gently on top of the Density Reagent in the settling chamber. In this regard, tilting the settling chamber/holder assembly at an angle (e.g. a 45-degree angle) allows for gentle dispense of the sample onto the Density Reagent.

The settling chamber/holder assembly is then loaded into a centrifuge and subjected to centrifugation for two minutes at 200 g, where "g" is a measure of the earth's gravitational force (i.e. $g=(1.118\times10^{-5})$ R $S^2$ where g is the relative centrifugal force, R is the radius of the rotor in centimeters, and S is the speed of the centrifuge in revolutions per minute). Centrifugation forces in the method described herein can vary from about 50 g to 500 g for about 0.5 to about 5 min. In one embodiment, the centrifugation force is about 50 g to 250 g for about 0.5 minutes to about 5 minutes. In another embodiment the centrifugation force is about 200 g for about 2 to about 3 minutes. In yet another embodiment, the centrifugation force is about 50 g for about 5 minutes. In another embodiment the centrifugation force is about 100 g for about 2 to about 5 minutes. In another embodiment the centrifugation speed is about 200 g for about 2 to 5 minutes. In another embodiment the centrifugation force is about 250 g for about 1 minute to about 3 minutes. Other ranges for centrifugation forces include 60 g to 490 g, 70 g to 480 g, 80 g to 470 g, 90 g to 460 g, 100 g to 450 g, 110 g to 440 g, 120 g to 430 g, 130 g to 420 g, 140 g to 410 g, 150 g to 410 g, 160 g to 400 g, 170 g to 390 g, 180 g to 380 g, 190 g to 370 g and 200 g to 360 g. Other time ranges include about 0.6 min to about 4.9 min, about 0.7 min to about 4.8 min, about 0.8 min to about 4.7 min, about 0.9 min to about 4.6 min, about 1 min to about 4.5 min, about 1.1 min to about 4.4 min, about 1.2 min to about 4.3 min, about 1.3 min to about 4.3 min, about 1.4 min to about 4.2 min, about 1.5 min to about 4.1 min, about 1.6 min to about 4 min, about 1.7 min to about 3.9 min, about 1.8 min to about 3.8 min, about 1.9 min to about 3.7 min, about 2 min to about 3.6 min, about 2.1 min to about 3.6 min, about 2.2 min to about 3.5 min, about 2.3 min to about 3.4 min, about 2.4 min to about 3.3 min, about 2.5 min to about 3.4 min, about 2.6 min to about 3.3 min, about 2.7 min to about 3.2 min, about 2.8 min to about 3.1 min and about 2.9 min to about 3 min. However, it was observed that centrifugation for 0.5 min or less results in a lack of cellularity on the slide (e.g. very few cells are formed on the slide). Centrifugation at lower forces (about 50 g) for longer times (about 5 minutes) were observed yield a slide with well-preserved and evenly distributed cells. Higher forces for longer times also provide good cellularity. However, forces greater than 200 g for an amount of times greater than 2 to 3 minutes or forces equal to or less than 50 g for times of about 5 minutes provide for an increased number of inflammatory cells. At centrifugation speeds of 100 g to 200 g, good saturation with little inflammation is obtained for centrifugation times of about 3 to about 5 minutes. In one embodiment centrifugation forces of 200 g to 250 g, with centrifugation times of 2 to 3 minutes are used.

In one embodiment, the settling chamber assembly illustrated in FIGS. 5 and 13 is placed in a centrifuge bucket, the bucket being adapted to be received by the centrifuge. Centrifuge buckets are well known to one skilled in the art and are not described in detail herein. In one embodiment, the centrifuge bucket is one designed for a 96-well microtiter plate. Such a bucket is well-suited to receive the settling chamber holder illustrated in FIG. 13. In another embodiment, the centrifuge bucket has a minimum diameter of about 9 cm. A bucket with a minimum diameter of about 9 cm will receive the settling chamber assembly of FIG. 5.

After centrifugation, the settling chamber/holder assembly is removed from the centrifuge and inverted over a sink or bin or other suitable receptacle to decant any remaining fluid sitting above the density reagent. After decanting, the assembly can be inverted for about a minute to ensure all excess material is removed. The density reagent and any other remaining material is removed from the slide by pipetting approximately 1 mL of 100% alcohol or an alcohol blend (e.g. BD Alcohol Blend Rinse from Becton Dickinson) into the settling chamber and further decanting over a sink or bin or suitable receptacle. Ethanol is an example of a suitable alcohol. This step may be repeated. In some embodiments, excess liquid is then blotted from the slide using absorbent paper. To avoid disturbing the cells that are attached to the slide, the pipette tip is pressed firmly against the inside of the settling chamber and the rinse is gently expelled from the pipette.

The settling chamber is then removed from the slide and holder and the slide carrying the attached cells is placed into a slide rack and immersed in 100% alcohol or alcohol blend rinse disposed in a suitable container for receiving and immersing the slide.

After the sample is prepared, the sample is stained and evaluated using conventional techniques. Non-limiting examples of suitable stains include cytology stain kits containing the Haematoxylin stain 0.75 and EA/OG stains from Becton Dickinson. An example of a non-gynecology stain kit includes Haematoxylin stain 0.5 and EA/OrangeG stains from the BD PrepStain® reagent kit.

In one embodiment, the following staining protocol is used. One of ordinary skill will appreciate that many different staining protocols are compatible with the methods described herein. For this exemplary staining protocol, the slides were prepared as described above. The prepared slides were placed in alcohol (e.g. alcohol used in the BD™ PrepStain® slide processor). The slides are rinsed in DI water for about 1 minute and then in a stain (e.g. Haematoxylin substitute) for about 90 seconds. Two rinses with DI water, for about 30 seconds each, followed by two alcohol rinses for about 30 seconds each, followed. The sample on the slide is then stained using stain (e.g. BD™ PrepStain® EA/OrangeG Combo Stain). This was followed by two alcohol rinses at about 30 seconds each. The slide was then placed in an organic solvent (e.g. xylene) for about 30 seconds after which the stained slide is placed in xylene until it is used.

Figure 6:
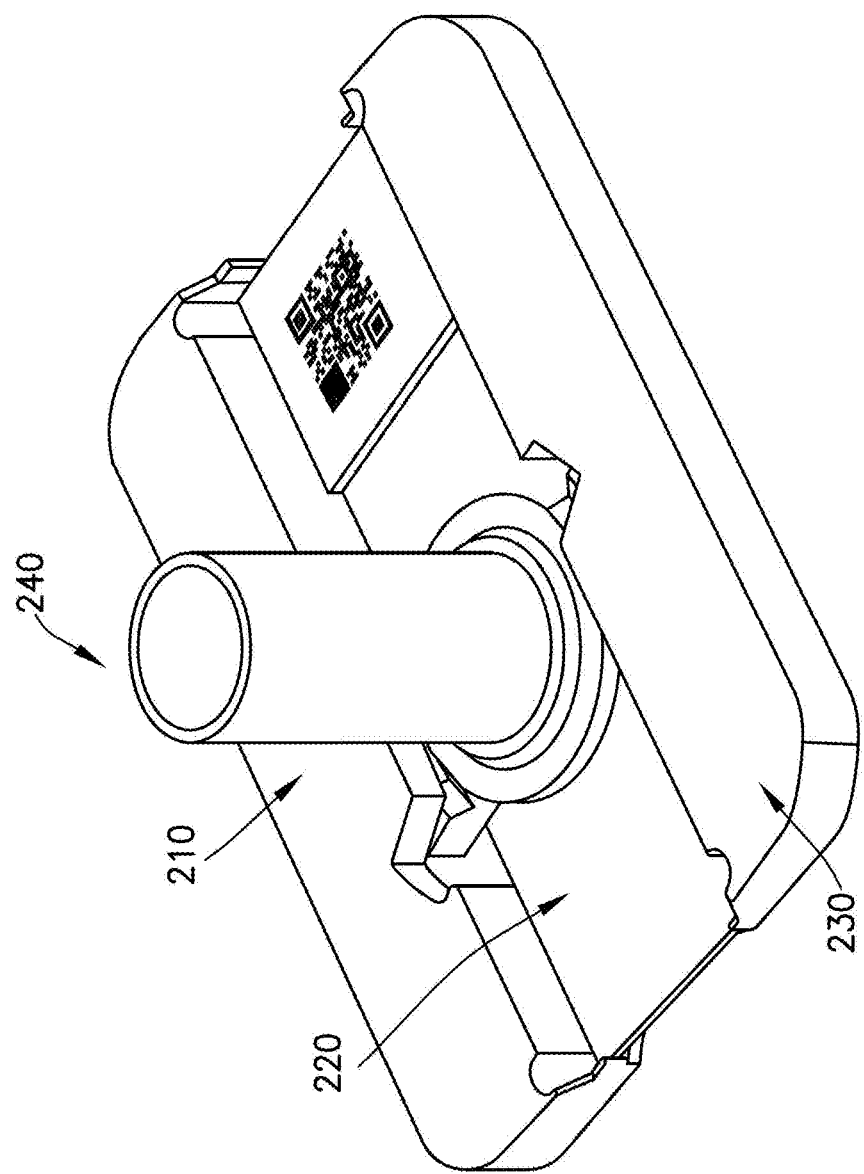
FIG. 6 illustrates the settling chamber prior to inoculation.
Figure 7:
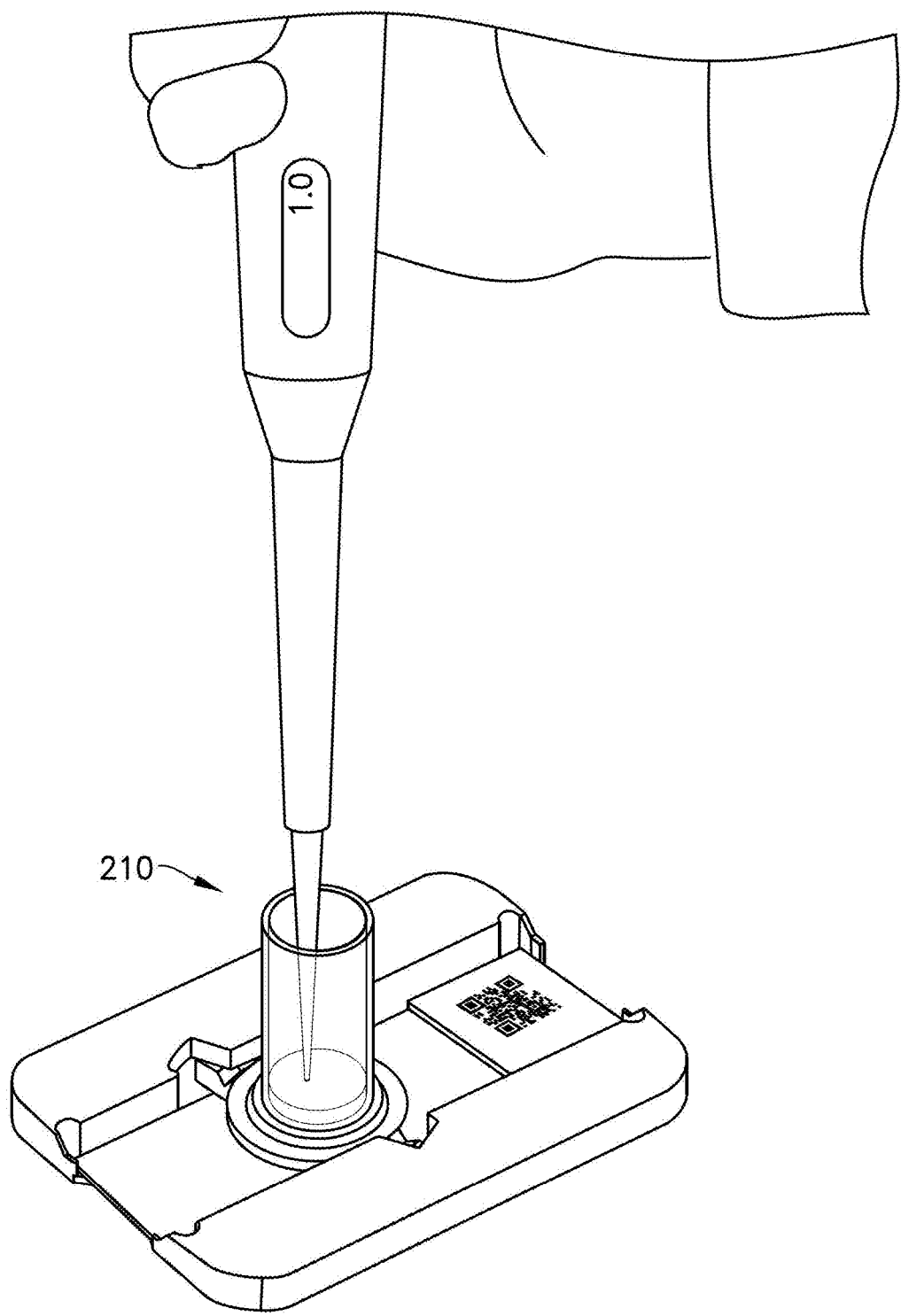
FIG. 7 illustrates adding the density reagent to the settling chamber.
Figure 8:
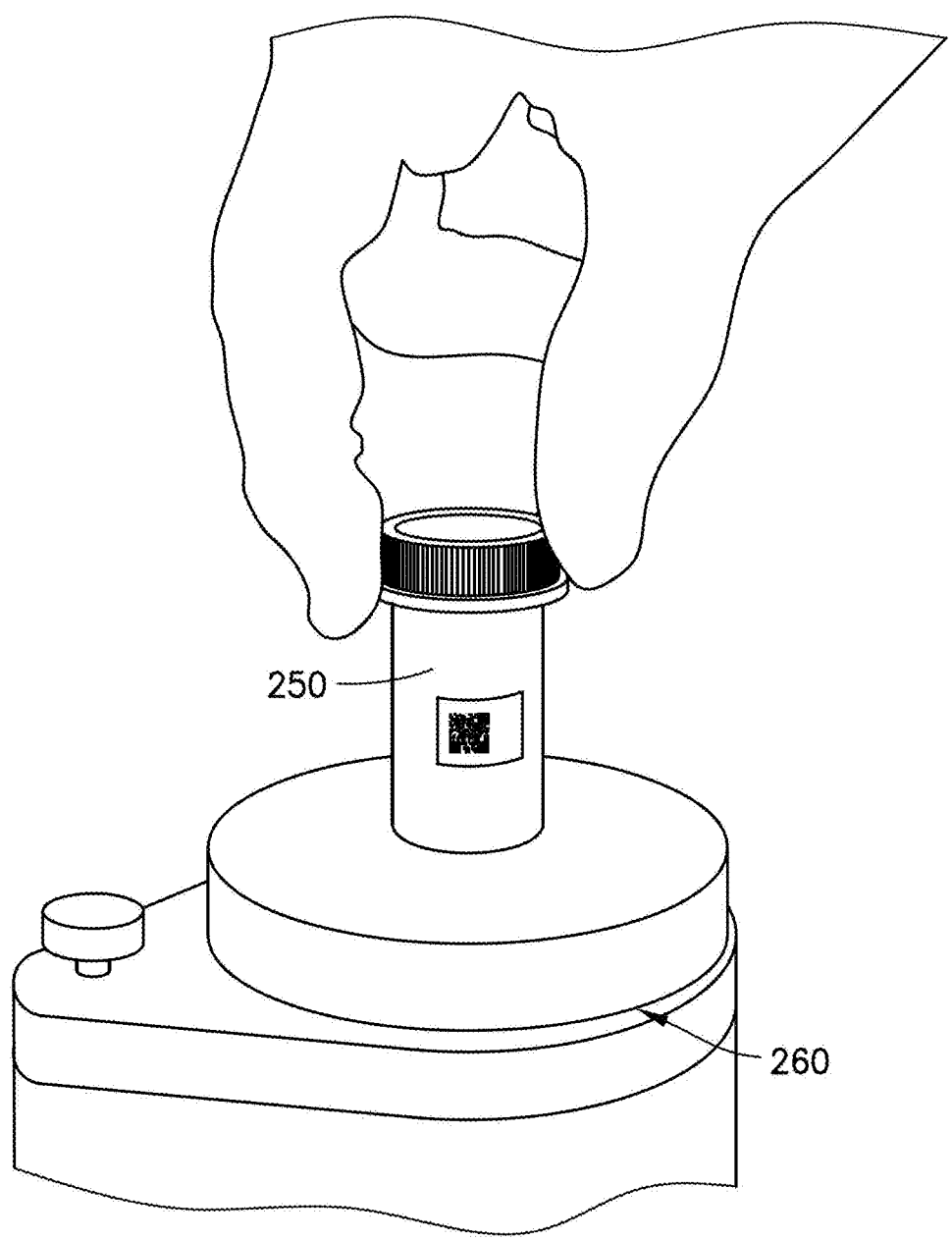
FIG. 8 illustrates vortexing the sample in a sample.
Figure 9:
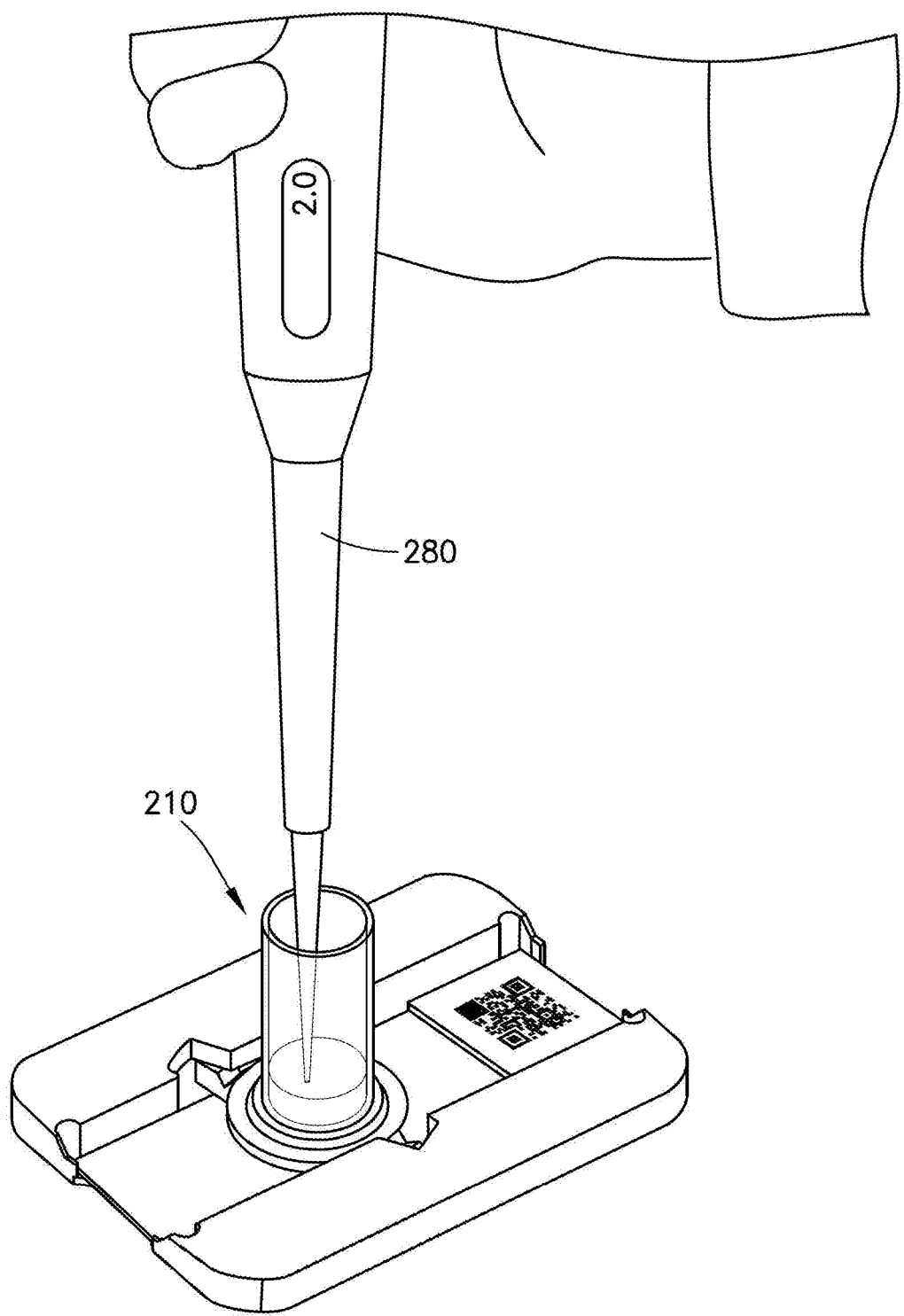
FIG. 9 illustrates adding sample to the density chamber.
Figure 10:
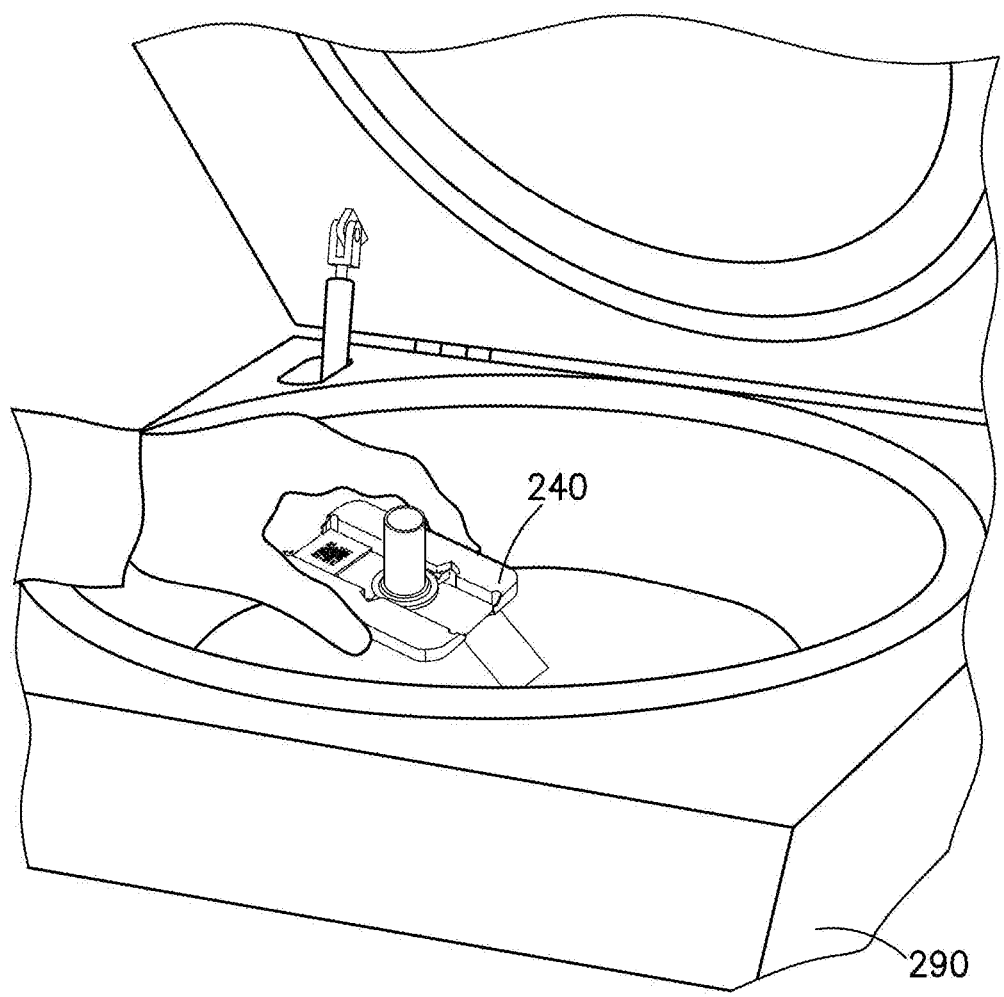
FIG. 10 illustrates placing the assembly in a centrifuge.
Figure 11:
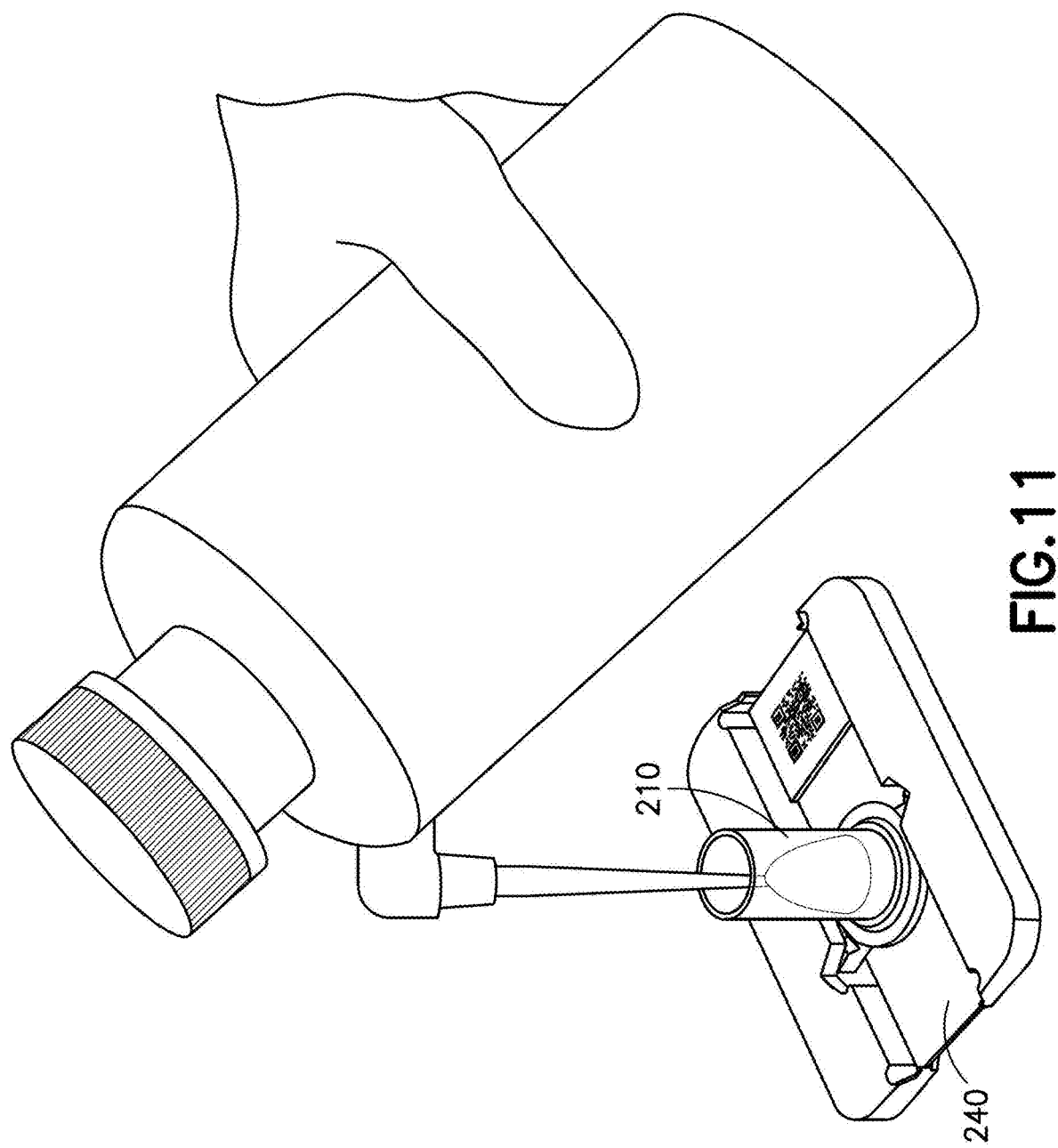
FIG. 11 illustrates rinsing the sample after centrifugation.
Figure 12:
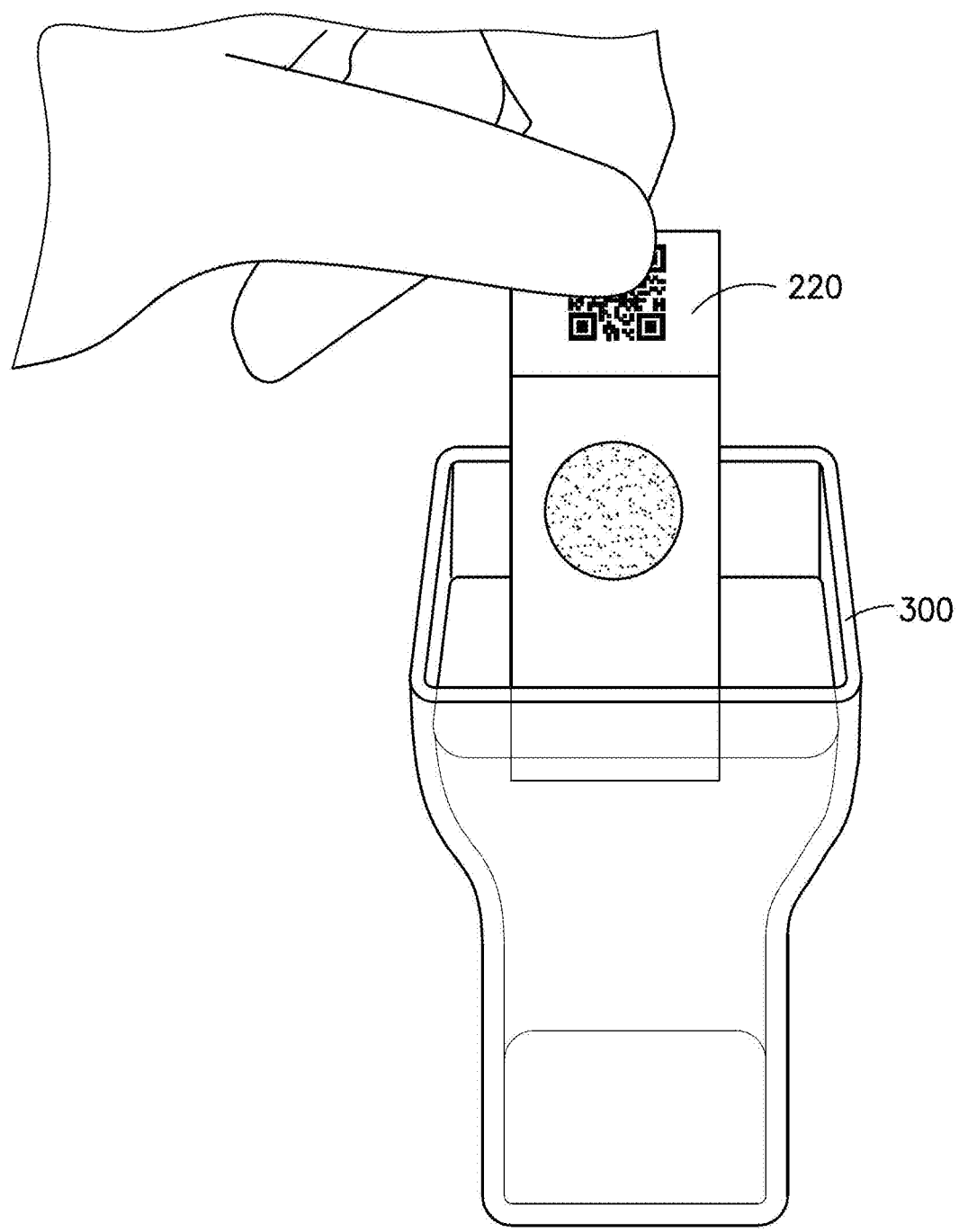
FIG. 12 illustrates washing the slide in an alcohol rinse prior to staining.

Referring to FIGS. 6 to 12, the method is described in terms of the various consumables and equipment used to practice the method. In one embodiment, the sample is collected using a Rovers® Cervex-Brush® or equivalent sampling device. The brush head is rinsed directly into the fluid. The brush head is removed and dropped into a collection vial containing, for example, BD SurePath™ resulting in an LBC sample. Referring to FIG. 6, a labeled slide 220 carrying the BD PreCoat™ is placed in the holder 230, after which a settling chamber 210 is affixed to the holder 230 to form holder assembly 240. About 1 mL of a Density Reagent is pipetted into the settling chamber 210 as illustrated in FIG. 7. Density Reagents are well known to those skilled in the art and include, but are not limited to herastarch, O-(2-hydroxyethyl)-aminopectin-hydrosylate, or Percoil, which are described in U.S. Pat. No. 5,346,831 which is incorporated by reference herein. Referring to FIG. 8, the collection vial 250 is vortexed for about 15 seconds in a vortexer 260. Sufficient volume is available in the collection vial to allow removal of up to 0.5 mL of homogenous mixture of cells and fluid for testing, but still allowing sufficient volume for Pap testing. Aliquoting of the sample onto the slide is performed after vortexing as illustrated in FIG. 9. Viewing FIG. 9, about 2 mL of the vortexed sample is pipetted into the settling chamber 210. The edge of the pipette tip 280 is held against the edge of the settling chamber 210 and care is taken not to disrupt the surface of the density reagent. FIG. 10 illustrates the slide kit holder assembly 240 being placed in a centrifuge 290. After centrifugation under the conditions described elsewhere herein, the holder assembly 240 is removed from the centrifuge, after which the contents of the density chamber are decanted and, as illustrated in FIG. 11, the sample remaining on the slide is washed by pipetting 1 mL of an alcohol blend rinse into the settling chamber 210. Again, the pipette is held against the side of the settling chamber 210 during this rinse to avoid dislodging the cells from the surface of the slide as illustrated in FIG. 11. The solution is decanted by inversion and this step is repeated. The slide holder 230 is then inverted for about a minute, after which the settling chamber 210 is removed from the holder. As illustrated in FIG. 12, the slide 220 is then placed in an alcohol rinse 300 after which the slide is stained.

Comparison with Other Methods

The above method was compared with several other methods. The above method was found to be superior in terms of image quality, ease of workflow, time to complete the method, cost of the reagents and consumables and the ease of implementation. For comparison, the following methods were evaluated: 1) Reduced Steps Method for liquid-based cytology (LBC); 2) Reduced Reagent Method for LBC; 3) Syringe Method optimal value system (OVS); and 4) Dual Flow Cassette method.

In the Reduced Steps Method, vials containing 8 mL of sample were vortexed. Prepstain® Density Reagent (DR) (4 mL) was pipetted into a centrifuge tube. The vial cap was removed and the 8 mL of sample was pipetted into the centrifuge tube containing the density reagent. The tube was centrifuged at a force of 200 g for 2 minutes after which 8 mL of the top fluid was aspirated from the centrifuge tube using Pasteur pipette. The tubes were then centrifuges at a force of 800 g for 10 minutes. The excess fluid was decanted but the cell pellet stayed in the tube. Deionized water (4 mL) was added to each tube containing the pellet and the tubes was vortexed to create a suspension. A SurePath™ PreCoat slide was placed into a slide rack and a Prepstain® settling chamber was locked onto each slide. The resuspended pellet (800 µl) was added to the settling chamber with the SurePath™ PreCoat slide underneath. The assembly with the suspension in the settling chamber was allowed to sit for 10 minutes for gravity settling. The remaining fluid was decanted from the settling chamber. The settling chamber was then rinsed with 1 mL of 100% alcohol, after which the settling chamber was decanted. The decant step was repeated, excess liquid was blotted away and the slides remained inverted for at least 1 minute. The slides were removed and stored in alcohol until they were stained. The staining protocol used is described elsewhere herein.

In the reduced reagent method sample and density reagent were added to each tube in the following proportions:

| Reduced Reagent proportions (sample (mL)/density reagent (mL)) | | | | |
|---|---|---|---|---|
| 4/2 | 2/1 | 8/1 | 4/4 | 2/4 |

Using a Pasteur pipette, the amount of sample was removed from a vial and dispensed slowly in a centrifuge tube containing the stated amount of density reagent. The tubes were centrifuged at a force of 200 g for 2 minutes. The fluid above the density reagent was removed using a Pasteur pipette. The tubes were then centrifuged at a force of 800 g for 10 minutes. The rack was held inverted to remove excess fluid and the tubes were blotted using absorbent paper. The cell pellet remained in the tube. Deionized water (4 mL) was added to each tube containing a pellet and the pellet and water were mixed by vortexing. A SurePath™ PreCoat slide was placed into a slide rack and a Prepstain® settling chamber was locked onto each slide. Sample (800 µl) was added into the settling chamber/precoated slide assembly. The suspension was allowed to gravity settle onto the slide for 10 minutes. The assembly was inverted to decant the remaining fluid from the settling chamber and excess liquid was blotted from the settling chamber using absorbent paper. The settling chambers were rinsed with 1 mL of 100% ethanol and the solution was decanted from the settling chamber. This process was repeated. The slides were removed from the settling chamber and allowed to air-dry). After drying, the slides were placed in a slide rack completely immersed in a container containing alcohol.

For the syringe method, a SurePath' PreCoat slide was placed into a slide rack. A Prepstain® settling chamber was locked onto each slide. Vials containing sample were vortexed. Sample (3 mL) was transferred to a syringe. The syringe was equipped with a filter. The sample was expelled from the syringe through the filter leaving 0.5 mL in the syringe. The sample was washed by drawing up and dispensing 3 mL of DI water, leaving about 0.5 mL at end of each dispense cycle. The wash was repeated three times. For the last wash, 1 mL of sample was left in the syringe and the filter was removed. Sample (1000 µl) was placed into a settling chamber/PreCoat slide assembly for each sample. The sample was allowed to settle onto the slide for 10 minutes. The settling chamber was inverted to decant the remaining fluid from the settling chamber. Any excess liquid was blotted out using absorbent paper. The settling chambers were rinsed with 1 mL of 100% alcohol. The rinse solution was decanted from the settling chamber. The rinse was repeated and the slides were inverted for at least 1 minute. The slides were allowed to air dry and then were placed in a slide rack completely immersed in alcohol. The slides were stained according to the protocol described elsewhere herein.

A dual flow cassette is a way to deliver a cytology sample onto hydrophobic slides without using a settling chamber. A low volume of sample (2 mL) is used and the sample is not centrifuged. The dual flow cassette filters the sample directly onto the slide. The amount of eluate deposited on the slide is about 0.5 mL. Once the sample is dispensed onto the slide, the slide is stained according to the staining protocol described herein.

Surprisingly, the method described herein is an improvement over the other method described herein in terms of consistently yielding satisfactory samples. Prior art methods are designed to avoid direct contact between the density reagent and the pre-coated slide. The present method allows for contact between the pre-coated slide and the density reagent without adverse effect. Specifically, the direct contact of the density reagent with the slide does not inhibit the ability of cells in the sample to adhere to the slide. Also, surprisingly, direct centrifugation of the sample through the density reagent, at the volumes described herein, produced slides with comparable diagnostic quality as those derived from the legacy multistep procedure set forth in FIG. 2. Specifically, using both methods, there was a marked reduction of inflammatory cells, red blood cells and random cellular debris and a subsequent enrichment of diagnostically relevant cells. Also, the cells were observed to retain sufficient cellularity required for clinical diagnostic use. Referring to FIG. 14 in this regard, slides were prepared using the prior art process of FIG. 2 and the process described herein and outlined in FIG. 3. After the samples cells were stained, images of the slides were obtained. The images of three slides using the process described in FIG. 3 are 310, 320 and 330 in FIG. 14. The images of three slides using the process described in FIG. 2 are 340, 350 and 360 in FIG. 14. There is virtually no difference in the appearance of the samples prepared by the two processes although the method described in FIG. 3 is far simpler than the method described in FIG. 2.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

The invention claimed is:

1. A method for preparing a cytology sample for staining, the method comprising:
    providing a biological sample, wherein the biological sample is a liquid-based cytology (LBC) sample;
    disposing a pre-coated slide in a holder adapted for receiving the pre-coated slide, the slide pre-coated with a composition that will cause cells to adhere to the pre-coated slide;
    placing a settling chamber over the pre-coated slide and locking the settling chamber onto the holder wherein the settling chamber has openings in both proximate and distal ends, wherein the opening in the distal end is positioned over the pre-coated slide such that the pre-coated slide is interposed between the holder and the settling chamber and the pre-coated slide is in fluid communication with the settling chamber;
    locking the settling chamber into place in the holder thereby forming an assembly of the holder, the pre-coated slide and the settling chamber;
    placing a density reagent into the settling chamber;
    adding the liquid-based cytology sample into the settling chamber over the density reagent;
    placing the assembly in a centrifuge;
    centrifuging the assembly once for about 5 minutes or less at a rotation force of about 500 g or less, wherein the method has only one centrifugation step;
    decanting, by inversion, the density reagent and the liquid-based cytology sample thereover from the settling chamber;
    removing the settling chamber from over the pre-coated slide; and
    staining the sample on the pre-coated slide.

2. The method of claim 1 wherein the assembly is centrifuged for about 0.5 to about 5 min at a rotation force of about 50 g to about 500 g.

3. The method of claim 2 wherein the assembly is centrifuged for about 0.5 minutes to about 5 minutes at a rotation force of about 50 g to about 250 g.

4. The method of claim 3 wherein the assembly is centrifuged for about 2 to about 3 minutes at a rotation force of about 200 g.

5. The method of claim 3 wherein the assembly is centrifuged for about 5 minutes at a rotation force of about 50 g.

6. The method of claim 3 wherein the assembly is centrifuged for about 2 to about 5 minutes at a rotation force of about 100 g.

7. The method of claim 3 wherein the assembly is centrifuged for about 2 to 5 minutes at a force of about 200 g.

8. The method of claim 3 wherein the assembly is centrifuged for about 1 minute to about 3 minutes at a force of about 250 g.

9. The method of claim 1 wherein the pre-coated slide is pre-coated with a polycationic coating.

10. The method of claim 9 wherein the polycationic coating is a non-peptidic, quaternary ammonium polymer.

11. The method of claim 10 wherein the non-peptidic, quaternary ammonium polymer comprises polydiallyldimethylammonium (PDDA).

12. The method of claim 1 wherein an amount of the liquid-based cytology sample placed in the settling chamber is about 1 mL to about 2 mL.

13. The method of claim 1 wherein an amount of density reagent is about 1 to about 4 mL.

* * * * *